(12) United States Patent
Oh et al.

(10) Patent No.: US 8,466,268 B2
(45) Date of Patent: Jun. 18, 2013

(54) ***LACTOBACILLUS* SP. JNU2116 WITH ANTIMUTAGENIC ACTIVITY**

(75) Inventors: Sejong Oh, Seoul (KR); Jonguk Jeong, Gwangju (KR); Sungsu Park, Seoul (KR); Sae Hun Kim, Seoul (KR); Yonghoon Kim, Namyangju-si (KR)

(73) Assignee: Industry Foundation of Chonnam National University, Yongbong-Dong, Gwangju (KR)

( * ) Notice: Subject to any disclaimer, the term of this patent is extended or adjusted under 35 U.S.C. 154(b) by 296 days.

(21) Appl. No.: 12/862,855

(22) Filed: Aug. 25, 2010

(65) Prior Publication Data

US 2011/0165134 A1    Jul. 7, 2011

(30) Foreign Application Priority Data

Jan. 7, 2010    (KR) ........................ 10-2010-0001315

(51) Int. Cl.
    *C07H 21/04*    (2006.01)
    *C07H 21/02*    (2006.01)
    *A61K 39/00*    (2006.01)

(52) U.S. Cl.
    USPC .................. 536/23.1; 435/6.1; 424/185.1

(58) Field of Classification Search
    None
    See application file for complete search history.

(56) References Cited

PUBLICATIONS

Rhee et al., Isolation and Characterization of Lactic Acid Bacteria Producing Antimutagenic Substance from Korean Kimchi, Kor J Appl Microbiol Biotechnol 27, 1 (1999) pp. 15-22.
Korean Office Action issued Sep. 16, 2011 in connection with Korean Patent Application Serial No. 10-2010-0001315 and Request for Entry of the Accompanying Office Action attached herewith.
R. Fuller, "Probiotics in man and animals", Journal of Applied Bacteriology 1989, 66, 365-378.
Yuan-Kun Lee et al., "The coming of age of probiotics", Trends in Food Science & Tecnology Jul. 1995 [vol. 6], pp. 241-245.
Bruce N. Ames et al., "Carcinogens are Mutagens: A Simple Test System Combining Liver Homogenates for Activation and Bacteria for Detection", Proc. Nat. Acad. Sci. USA, vol. 70, No. 8, pp. 2281-2285, Aug. 1973.
Dorothy M. Maron et al., "Revised methods for the *Salmonella* mutagenicity test", Mutation Research, 113 (1983) 173-215.

*Primary Examiner* — Vanessa L Ford
*Assistant Examiner* — Nina Archie
(74) *Attorney, Agent, or Firm* — Robert E. Bushnell, Esq.

(57) ABSTRACT

*Lactobacillus* sp. strain with antimutagenic activity and, more particularly, *Lactobacillus* sp. JNU2116 having a specific amino acid sequence at an N-terminal. Such strain has various advantages in that it has antimutagenic activity to inhibit mutation of cells thus preventing cancer caused by modification of genes, may be added to general fermented dairy products, food additives and/or health foods so as to be simply applied to the human body by the intake of food and, in addition, may be safely used without side effects from intake thereof. The strain was deposited with Accession No. KCCM11055P to Korea Culture Center of Microorganisms (KCCM) (having the address of 361-221, Yurim B/D. Hongje-1-dong, Seodaemun-gu, Seoul, 120-091, Republic of Korea) on Dec. 2, 2009.

6 Claims, 3 Drawing Sheets

SEQUENCE LISTING

<160> NUMBER OF SEQ ID NOS: 4

<210> SEQ ID NO 1
<211> LENGTH: 202
<212> TYPE: DNA
<213> ORGANISM: Lactobacillus sp.

<400> SEQUENCE: 1
gcgactgctc tggttatacc gtcatacctg aacagttact ctcagatatg ttcttcttta      60
acaacagagt tttacgagcc gaaaccttc ttcactcacg cggcgttgct ccatcagact     120
ttcgtccatt gtggaagatt ccctactgtc gcctcccgta gggggcggg ggcggcgggc     180 cgggcgcggg gcgcggcggg gg                                             202

<210> SEQ ID NO 2
<211> LENGTH: 14
<212> TYPE: PRT
<213> ORGANISM: Lactobacillus sp.
<220> FEATURE:
<221> NAME/KEY: misc_feature
<222> LOCATION: (1)..(1)
<223> OTHER INFORMATION: Xaa can be any naturally occurring amino acid
<220> FEATURE:

```
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid

<400> SEQUENCE: 2

Xaa Leu Glu Xaa Lys Lys Ala Glu Xaa Ile Thr Thr Xaa Xaa
1               5                   10

<210> SEQ ID NO 3
<211> LENGTH: 18
<212> TYPE: DNA
<213> ORGANISM: Artificial Sequence
<220> FEATURE:
<223> OTHER INFORMATION: Forward Primer for PCR of Lactobacillus sp.
      JNU2116

<400> SEQUENCE: 3
gagtttgatc ctggctca                                                   18

<210> SEQ ID NO 4
<211> LENGTH: 20
<212> TYPE: DNA
<213> ORGANISM: Artificial Sequence
<220> FEATURE:
<223> OTHER INFORMATION: Reverse Primer for PCR of Lactobacillus sp.
      JNU2116

<400> SEQUENCE: 4
agaaaggagg tgatccagcc                                                 20
```

LACTOBACILLUS SP. JNU2116 WITH ANTIMUTAGENIC ACTIVITY

RELATED APPLICATIONS AND CLAIM OF PRIORITY

This application claims priority from Korean Patent Application No. 2010-0001315 filed on Jan. 7, 2010 in the Korean Intellectual Property Office, the entire disclosure of which is incorporated herein by reference.

BACKGROUND OF THE INVENTION

1. Field of the Invention

The present invention relates to *Lactobacillus* sp. strain with antimutagenic activity.

2. Description of the Related Art

Probiotics refers to live microorganisms that are administered to humans or animals in order to improve balance between intestinal bacteria, in turn enhancing health of a host (Fuller, R. Probiotics in man and animals, 1989, J. Appl. Microbiol. 66: 365-378). Health enhancing effects of probiotics may include balancing and maintaining microflora, stimulation of an immune system, anticarcinogenic activity, and the like. The probiotics are generally contained in a nutrition agent or administered in a capsule form and should satisfy some requirements including, for example: survival in a digestive tract under general conditions (such as low pH inside the stomach, acid exist in a digestive system, etc.); correct adhesion to a bowel wall; intestinal metabolism; practical applicability (tolerance to operation); expression of favorable health effects reported after clinical trial; intake safety and so forth (Salminen, S, et al. 1995, The coming age of probiotics. Trend Food Sci Technol, 6: 241-245).

In view of taxonomic system, *Lactobacillus* refers to a spherical or rod type microorganism that is gram-positive, catalase-negative, neither forms spore nor uses cytochrome as an electron donor, and exhibits reduced tolerance to oxygen and low pH. In addition, the *Lactobacillus* strain which ferments hydrocarbon and generates lactic acid as a final product of metabolism is a representative microorganism to ensure improvement of health in nutritional-physiologic aspects, that is, control of intestinal behavior, inhibition of pathogenic bacteria, promotion of digestion and absorption, prevention of constipation and irregularity diarrhea, etc., thus being effectively employed in various applications including, for example: fermented milk products; naturally fermented foods; a treatment for digestive tract disease of human or animals; livestock feeds; pharmaceutical applications, and so forth.

Meanwhile, as the most serious disease to threaten health of humans in modern society, cancer occurs in general by activation of tumor generating genes when genes are modified. Since a variety of chemical carcinogens and dietary factors influences genes through different routes, cancer incidence and mortality are continuously increased in spite of medical development. Therefore, identification of causes and/or mechanisms of cancer generation should still be accomplished (Ames, B. N., et al., 1973, Proc. Net. Acad. Sci. USA., 70, 2281-2285).

In Korea, stomach cancer incidence and liver cancer incidence are remarkably higher than those in other advanced countries, and we believe this is because of typical Korean dietary habits and/or living habits influencing such diseases. Therefore, foods and nutritional substances have been suggested as the most significant parameter among various causes of cancer.

As to prevention and treatment of cancer, a great deal of research and investigation into various functional foods with immune activity to the human body or anticarcinogenic effects is currently conducted.

SUMMARY OF THE INVENTION

According to an aspect of the invention, one or more embodiments of the present invention include a *Lactobacillus* sp. strain that was deposited with Accession No. KCCM11055P to Korea Culture Center of Microorganisms (KCCM) (having the address of 361-221, Yurim B/D. Hongje-1-dong, Seodaemun-gu, Seoul, 120-091, Republic of Korea) on Dec. 2, 2009.

Another aspect of the present invention is to provide a food composition, a fermented food product and a health food with cancer prevention and suppression effects, each of which includes the foregoing strain or a cultured product thereof and exhibits antimutagenic activity.

According to an aspect of the invention, one or more embodiments of the present invention includes an in vitro culture including *Lactobacillus* sp. JNU2116 having a sequence represented by SEQ ID No: 1, the accession number of the deposit of *Lactobacillus* sp. JNU2116 being KCCM11055P.

According to an aspect of the invention, a method of inhibiting mutation of cells in a subject includes administering a composition to the subject, the composition including *Lactobacillus* sp. JNU2116, the accession number of the deposit of which is KCCM11055P.

*Lactobacillus* sp. JNU2116 of an embodiment of the present invention exhibits favorable antimutagenic activity to inhibit mutation of cells and, when added to fermented dairy products, food additives and/or health foods, can prevent or suppress cancer caused by modification of genes.

In addition, *Lactobacillus* sp. JNU2116 or a cultured product thereof according to an embodiment of the present invention may be easily applied to health foods or food compositions, etc. without adverse effects from intake thereof.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION

The present inventors found that a specific *Lactobacillus* sp. strain containing a particular amino acid sequence may have antimutagenic activity to inhibit mutation of cells, thus preventing activity of carcinogens or detoxifying the same while safely being added to general food products. Therefore the present invention has been accomplished.

One or more embodiments of the present invention is directed to a *Lactobacillus* sp. strain with antimutagenic activity and, in particular, provides *Lactobacillus* sp. JNU2116 having a specific amino acid sequence at an N-terminal thereof, with advantages in that it has antimutagenic activity to inhibit mutation of cells thus preventing cancer caused by modification of genes, may be added to general fermented dairy products, food additives and/or health foods so as to be simply applied to the human body by the intake of food and, in addition, may be safely used without side effects from intake thereof.

Hereinafter, one or more embodiments of the present invention will be more apparent from the following detailed description.

*Lactobacillus* sp. JNU2116 having a sequence represented by SEQ ID NO: 1 according to an embodiment of the present invention has been isolated from Kimchi, a Korean traditional fermented food. Also, chromosome DNA isolation, 16S rDNA amplification, polymerase chain reaction (PCR) purification and DNA sequencing of such strain have been identified in sequential order. The strain was deposited with Accession No. KCCM11055P to Korea Culture Center of Microorganisms (KCCM) (having the address of 361-221, Yurim B/D. Hongje-1-dong, Seodaemun-gu, Seoul, 120-091, Republic of Korea) on Dec. 2, 2009.

Figure 2:
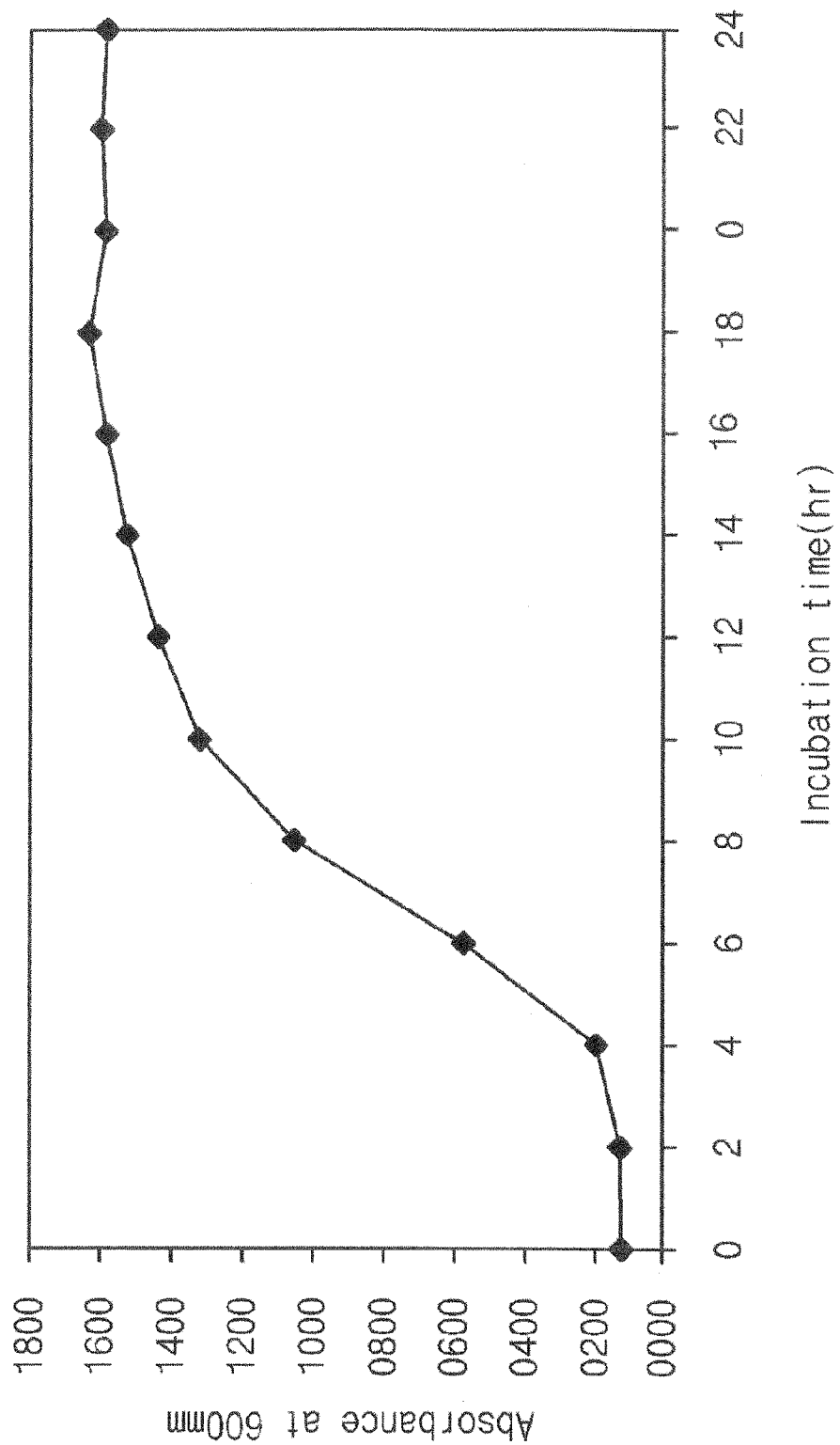
FIG. 2 illustrates variation in absorbance over culture time of *Lactobacillus* sp. JNU2116.

As a result of sequence analysis, it was found that the sequence was identified as *Lactobacillus plantarum* with 98% probability. After culturing at 37° C. for 18 hours, the cultured material was dispensed into 96-well microplates with 200 μl/well while secondly culturing the same, and the absorbance of the dispensed material was measured at every 2 hours for 24 hours. From the measured results, a growth curve was defined as shown in FIG. 2. As to variation in absorbance values, since the absorbance value was continuously increased in a region of 14 to 16 hours, a proper culturing time may range from 14 to 16 hours.

Figure 1:
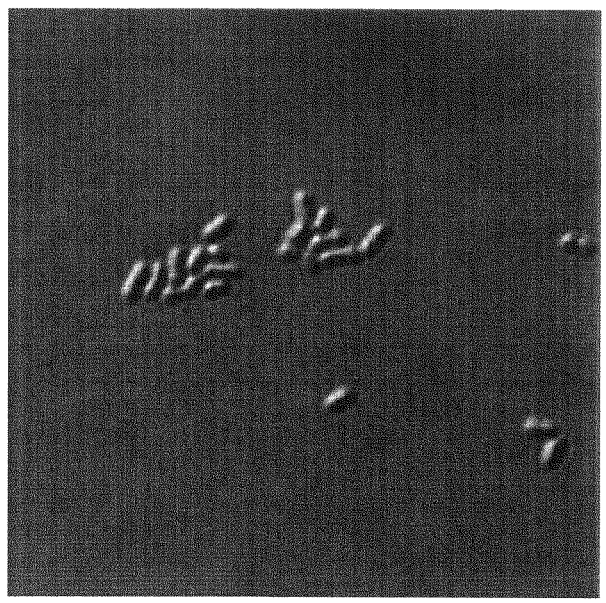
FIG. 1 is a microphotograph of *Lactobacillus* sp. JNU2116.

*Lactobacillus* sp. JNU2116 of the present invention (that is, *Lactobacillus plantarum* JNU2116) is in a *Bacillus* form that belongs to general lactobacilli, as shown in FIG. 1, a colony color of which is ivory white and wherein it is positive, negative and negative in gram staining reaction, catalase reaction and potassium hydroxide reaction, respectively.

*Lactobacillus* sp. JNU2116 of the present invention exhibits inhibitory effect of mutation activity by protein substances in a molecular weight range of 3 kDa or less and, especially, since a specific amino acid sequence of Xaa-Leu-Glu-Xaa-Lys-Lys-Ala-Glu-Xaa-Ile-Thr-Thr-Xaa-Xaa (SEQ ID NO: 2) is present at an N-terminal, the inventive JNU2116 shows inhibitory effects of mutation activity. Such Xaa refers to an amino acid.

An embodiment of the present invention provides a food composition, a fermented food and/or a cancer preventing composition including the inventive strain or a cultured product thereof.

Food referred to herein means a natural or processed product containing at least one nutrient and, preferably, a directly edible product after processing. Examples of the food may include fruits, vegetables, dried or cut fruits or vegetables, fruit juice, vegetable juice, a mixture thereof, chips, noodles, processed stock farm food products, processed marine food products, processed dairy products, fermented food products, bean food products, grain food products, microorganism-fermented food products, confectionery and bakery products, seasonings, processed meat products, acidic beverage, licorice roots and herbs, etc., however, is not particularly limited thereto. The foregoing food product of an embodiment of the present invention may further contain any additional component without particular limitation thereto in addition to a necessary ingredient such as the foregoing strain, a cultured broth, a concentrate or a dried substance of the cultured broth, or a probiotic agent, with a desired fractional ratio. Like conventional food products, different flavors and/or carbohydrates may be added as additional substances to the foregoing inventive food products, without particular limitation thereto. The strain, a cultured broth thereof, a concentrate or a dried substance of the cultured broth and/or the probiotic agent may be added to a raw material for manufacturing various food products such as foods, beverages, health drinks, gum, tea, vitamin complex, health foods, etc. or may be preferably admixed with cooked food. Also, food-scientifically acceptable supplementary additives may be further added together with the foregoing materials. Here, the strain, a cultured broth thereof, a concentrate or a dried substance of the cultured broth and/or the probiotic agent may be added in an amount of 0.01 to 90% by weight ("wt. %") relative to a total weight of the food. For a beverage, the above amount may range from 0.02 to 20 g and, preferably, 0.5 to 10 g relative to 100 mL of the beverage.

A fermented food referred to herein means a food prepared by adding at least one or two of microorganisms such as lactic acid bacteria, yeast, etc. to a food and fermenting the food through activity of the microorganism. More particularly, the fermented food refers to a food prepared by adding seed bacteria for fermentation to a food substance and ageing the same. Such fermented food may include all non-pasteurized open type fermented food products such as alcoholic liquors, breads, Kimchi, salted foods, soybean pastes, soy sauce, cheese, butter, yogurt, etc. In addition, the foregoing strain, a cultured broth thereof, a concentrate or a dried substance of the cultured broth, and the probiotic agent may be used as seed bacteria for food fermentation and, preferably, an inoculum for Kimchi. An amount of the seed bacteria may be suitably adjusted on the basis of types of fermented food and types of seed bacteria. Preferably, 0.0001 to 0.01 wt. parts (wet weight) of the seed bacteria relative to 100 wt. of a main food material may be inoculated.

According to an exemplary embodiment of the present invention, as to selection of a desired concentration of mutagen suitable for testing antimutagenic effects, experiments at every concentration were repeated three times and the number of natural revertant colonies was compared to the number of histidine revertant colonies formed after addition of the mutagen. If the number of histidine revertant colonies is larger than the number of natural revertant colonies, it means improved mutation effects. Therefore, an appropriate concentration of mutagen may be selected in consideration of shapes of formed colonies.

Hereinafter, the following examples will be given for concretely describing the present invention, however, these should not be construed as restricting the scope of the present invention.

EXAMPLE 1

Isolation and Identification of *Lactobacillus* Strain (1) Preparation of Bacteria and Isolation of Chromosome DNA

*Lactobacillus* sp. JNU2116 was sub-cultured at 37° C. for 16 to 18 hours using an MRS medium, followed by centrifugation at 3,000 rpm for 15 minutes, so as to generate a cell precipitate. After washing the cell precipitate twice using sterilized saline, the same was added to 1.5 mL Eppendorf tube in which 1 ml of medium containing 10% skim milk, 2% lactose and 0.3% yeast extract was included, the Eppendorf tube was placed in a lyophilizer at 80° C. and used for experiment.

After sub-culture of the bacteria in the MRS medium, 1.5 ml of bacteria was centrifuged at 8,000 rpm for 1 minute to produce pellets. The pellets were washed twice using 0.85% sodium chloride solution. Using 0.5 ml of lysozyme (10 mg/ml), the pellets were treated and cultured in a water bath at 37° C. for 1 hour. The cultured material was subjected to treatment using 20 μl of Protenase K (10 mg/ml) and 25 μl of 10% sodium dodecyl sulfate (SDS) and then culturing in a water bath at 60° C. for 30 minutes. Then, the cultured product was suspended in P:C:I solution containing phenol:chloroform:isoamyl alcohol with a relative ratio of 25:24:1, followed by centrifugation at 4° C. and 14,000 rpm for 3 minutes. From the treated mixture, a supernatant was separated and used. These procedures were repeated. 3M ammonium acetate solution ($NH_3OAc$) (pH 4.8) in ½ amount of the supernatant and 100% alcohol with twice the amount of the supernatant were added to the supernatant. After keeping the mixture at −20° C. for 1 hour, it was subjected to centrifugation at 4° C. and 14,000 rpm for 15 minutes. Pellets were observed, and a supernatant was completely removed. After adding 1 ml of 70% ethanol to the pellets, the mixture was suspended and centrifuged at 4° C. and 14,000 rpm for 5 minutes, a supernatant was removed, and the remaining product was dried at room temperature for 20 minutes. After using 100 μl of distilled water to dissolve the pellets, the solution was treated using 1 μl/of RNase A (10 mg/ml) and incubated at 37° C. for 1 hour. Using 0.8% agarose gel, electrophoresis was conducted to identify DNA.

(2) Amplification and Purification of 16r DNA

In order to amplify 16r DNA, a pair of primers having a sequence in SL-1 direction (forward direction): 5'-GAG TTT GAT CCT GGC TCA G-3' (SEQ ID NO: 3) and another sequence in SL-2 direction (reverse direction): 5'-AGA AAG GAG GTG ATC CAG CC-3' (SEQ ID NO: 4), was used to conduct polymerase chain reaction.

To polymerase chain reaction-premix (PCR-Premix, Bioneer), 1 μl of primer, 17 μl of sterile water and 1 μl of DNA extracted as described above were added and well admixed together. Under the following conditions stated in TABLE 1, polymerase chain reaction was conducted, and electrophoresis was performed using 1% agarose gel so as to detect protein bands.

TABLE 1

|  | 94° C. | 5 minutes | 1 cycle |
|---|---|---|---|
| Modification | 94° C. | 30 seconds | 35 cycle |
| Relaxation | 55° C. | 30 seconds |  |
| extension | 72° C. | 40 seconds |  |
|  | 72° C. | 7 minutes | 1 cycle |

The foregoing polymerase chain reaction product was purified using a PCR product purification kit (Intron). After sufficiently blending 20 μl of a sample with 500 μl of a buffer solution, the mixture was cultured at room temperature for 1 minute. The cultured material was transferred to a spin column tube and centrifuged at 13,000 rpm for 1 minute. After adding 700 μl of a washing buffer thereto, centrifugation was conducted again under the same conditions. Following this, 30 μl of an elution buffer was added and centrifuged. Electrophoresis was conducted using an agarose gel to identify DNA and sequence analysis was performed for purified DNA through chromatogram file program (SEQ ID No: 1).

EXAMPLE 2

Preparation of Mutagen

Each mutagen was tested according to Ames test. 4-nitroquinoline 1-oxide (4-NQO: Sigma-Aldrich Inc., St. Louis. MO. US) was diluted into 0.005 to 50 μg per 100 μl and used. Alternatively, N-methyl-N'-nitro-N-nitrosoguanidine (MNNG: Tokyo Chemical Industry Co.) was diluted into 0.05 to 50 μg per 100 μl and used. Also, 2-amino-3-methylimidazo [4.5-f]quinoline (IQ: Wako Pure Chemical Co.) was diluted into 0.1 to 50 μg per 100 μl and used. In order to select a desired concentration for the present experiment, the number of histidine revertant colonies based on concentration of mutagen and the number of natural revertant colonies (that is, spontaneous colonies) were measured.

For assessment of a direct mutagen, 500 μl of 0.2M sodium phosphate buffer (pH 7.4) was used. On the other hand, an indirect mutagen required for metabolically active material was assessed using 500 μl of S9 mixture, thus identifying histidine revertant colonies. *Salmonella Typhimurium* TA100 strain placed on a master plate, another strain incubated in a sterilized test tube for 14 to 16 hours (1 to $2\times10^9$ cells/mL) and 100 μl mutagen were fed into a cap tube. After lightly vortexing the mixture for 3 to 5 seconds, the cap tube was preliminarily incubated in a shaking water bath at 37° C. for 30 minutes. 1 mL of 0.5 mM histidine/biotin solution was added to 10 mL of top agar at 45° C. and each 3 ml of the mixture was dispensed into the cap tube after preliminary incubation and, after lightly vortexing for 3 to 5 seconds, the number of histidine revertant colonies was counted by spreading the treated material over a GM agar plate (that is, a minimal glucose plate) and culturing the same in an incubator at 37° C. for 48 hours.

For the number of spontaneous colonies, the procedures for measuring the number of histidine revertant colonies were repeated except for mutagen substances.

EXAMPLE 3

Assessment of Mutagen Inhibitory Activity of *Lactobacillus* sp.

(1) Preparation of S9 Aliquot and S9 Mixture

To a Sprague-Dawley male rat with a weight of about 200 g, 500 mg of Aroclor 1254 (Supeldo Inc) dissolved in 1 kg of corn oil was IP injected and, after 5 days, the rat was fasted for 12 hours before liver excision except for water. After cervical dislocation, the liver was excised under aseptic conditions and repeatedly washed using 0.15M cold KCl at 4° C., so as to completely eliminate impurities from the liver. 3 ml of 0.15M KCl solution was added to each 1 g of the clean liver and the liver was finely cut using sterile scissors, followed by homogenation and centrifugation at 4° C. and 9,000 rpm for 15 minutes. A supernatant of the centrifuged product was isolated and referred to as S9 aliquot. The S9 aliquot was stored in a deep freezer at −80° C.

In the present experiment, a standard S9 mixture was used. The S9 mixture was prepared by adding 2.0 mL of S9 aliquot (4%), 1.0 mL of $MgCl_2$—KCl salt, 0.25 mL of 1M glucose-6-phosphate (Sigma-Aldrich Co., St. Louis, Mo., USA), 2.0 mL of 0.1M NADP (Amresco, Inc), 25 mL of 0.2M phosphate buffer (ph 7.4) and 19.75 mL of distilled sterile water to 50 mL of the mixture, in reverse order.

(2) Assessment of Antimutagenic Activity

According to Maron and Ames method (Maron, D. M. and B. N. Ames. 1983. Revised methods for the *Salmonella* mutagenicity test. Mutation Research. 113:173-215, which is incorporated herein by reference), antimutagenic effects were examined by Ames test. Each experiment was repeated three times and an average value thereof was used in calculation. Materials used in the experiment were stored in separate cap tubes during testing. For 4-NQO and MNNG as direct mutagens, 500 ml of 0.2M sodium phosphate buffer (pH 7.4) was used. For IQ as an indirect mutagen, 500 mL of S9 mixture, 100 μl of a strain obtained by incubating *Salmonella Typhimurium* TA100 placed on a master plate in a sterilized test tube for 14 to 16 hours, 50 μl of *Lactobacillus* cytoplasm and 100 μl of mutagen were individually added to a cap tube and, after lightly vortexing the tube for 3 to 5 seconds, this mixture was preliminarily incubated in a water bath at 37° C. for 30 minutes. One milliliter of 0.5 mM histidine/biotin solution was added to 10 mL of top agar at 45° C., and this solution was dispensed into the cap tube after preliminary incubation and, after lightly vortexing for 3 to 5 seconds, the number of histidine revertant colonies was counted by spreading the treated material over a GM agar plate and culturing the same in an incubator at 37° C. for 48 hours. Based these results, inhibitory rate (%) was estimated.

$$\text{Inhibitory rate}(\%) = \frac{M - A}{M - S} \times 100$$

wherein M is the number of revertants derived from mutagen, A is the number of revertants remained after treatment of *Lactobacillus*-sonicated supernatant, and S is the number of natural revertants when the mutagen and *Lactobacillus*-sonicated supernatant are not used.

As a result, the number of revertant colonies obtained using 4-NQO was 301±7, and an inhibitory rate was 2.15%. On the other hand, when using MNNG, the number of revertant colonies was 716±8, and an inhibitory rate was 5.80%. Alternatively, if using IQ, the number of revertants was 118±3 and an inhibitory rate was 34.54%. (See TABLE 2.)

TABLE 2

Antimutagenic activity of *Lactobacillus* sp. JNU2116 to mutagen

| Mutagen | Sample | Revertant/plate (inhibitory rate %) |
| --- | --- | --- |
| 4-NQO | Control | 305 ± 10 |
| | Natural revertant (spontaneous) | 119 ± 4 |
| | *Lactobacillus* sp. JNU2116 | 301 ± 7 (2.15%) |
| MNNG | Control | 754 ± 19 |
| | Natural revertant (spontaneous) | 105 ± 5 |
| | *Lactobacillus* sp. JNU2116 | 716 ± 8 (5.80%) |
| IQ | Control | 140 ± 2 |
| | Natural revertant (spontaneous) | 76 ± 1 |
| | *Lactobacillus* sp. JNU2 116 | 118 ± 3 (35.54%) |

(3) Experiments of Influence of Additional Substance

With regard to a nutrient broth used for culture of *Salmonella Typhimurium* TA100 strain, an MRS medium used for culture of *Lactobacillus* sp. JNU2116 and dimethylsulforxide (DMSO) used for dilution of mutagen, influence of these materials upon antimutagenic test results was examined. According to Maron and Ames method, an Ames test was conducted by the same procedures as those used for the antimutagenic experiment except that a nutrient broth, an MRS medium and DMSO were added in amounts of 100 μl, 50 μl and 50 μl, respectively, instead of *Lactobacillus* sp. JNU2116 cytoplasm components, in order to count the number of histidine revertant colonies. The results of the antimutagenic activity of additional substance to mutagen MNNG are shown in TABLE 3.

TABLE 3

Antimutagenic activity of additional substance to mutagen MNNG

| Additional substance | Sample | Revertant/plate (inhibitory rate %) |
| --- | --- | --- |
| Nutrient broth | Control | 821 ± 13 |
| | Natural revertant (spontaneous) | 137 ± 3 |
| | Control nutrient broth | 814 ± 19 |
| MRS medium | Control | 602 ± 4 |
| | Natural revertant (spontaneous) | 143 ± 2 |
| | Control nutrient broth | 700 ± 15 |
| DMSO | Control | 1166 ± 70 |
| | Natural revertant (spontaneous) | 125 ± 9 |
| | Control nutrient broth | 1121 ± 60 |

EXAMPLE 4

Purification of Substances with Mutation Inhibitory Activity (1) Protease Treatment 50 μl of *Lactobacillus* sp. JNU2116 cytoplasm component and 10 μl (71500 units/mL) of a trypsin solution prepared by dissolving 0.005 g of trypsin (Sigma-Aldrich Co.) in 1 mL of $3^{rd}$ distilled sterile water were introduced into an Eppendorf tube and, after vortexing for 20 minutes, reaction was carried out in an incubator at 37° C. for 3 hours. Using IQ, it was determined as to whether or not mutagenic activity had disappeared.

As to *Lactobacillus* sp. JNU2116 cytoplasm component, it was found that the number of *lactobacillus* cytoplasm component colonies obtained after trypsin treatment is substantially identical to the number of colonies in the control. As a result, it was believed that a protein component influences antimutagenic activity.

The results of the antimutagenic activity to mutagen IQ of *Lactobacillus* sp. JNU2116 after trypsin treatment as well as *Salmonella Typhimurium* are shown in TABLE 4.

TABLE 4

Antimutagenic activity to mutagen IQ of *Lactobacillus* sp. JNU2116 after trypsin treatment as well as *Salmonella Typhimurium*

| Sample | Revertant/plate (inhibitory rate %) |
| --- | --- |
| Control | 148 ± 4 |
| Natural revertant (spontaneous) | 94 ± 1 |
| *Lactobacillus* sp. JNU2116 | 148 ± 3 (0%) |

(2) Purification of Mutation Inhibitory Activity Material

In order to extract *Lactobacillus* sp. JNU2116 cytoplasm component, 1 mL of Lysis buffer (40 mM Tris, 1 mM EDTA) was added to a cell precipitate from 10 mL of MRS culture broth containing cells obtained after centrifugation, followed by sonication for 15 minutes in an ice bath using a sonicator (Sonics & Materials, INC., USA) under desired conditions such as a wave width of 35%, a pulse on time of 3 seconds and a pulse off time of 5 seconds. The sonicated material was centrifuged, and a supernatant was isolated therefrom and used as a sample while storing the same in a deep freezer at −80° C.

50 μl of *Lactobacillus* sp. JNU2116 cytoplasm component and 10 μl (71500 units/mL) of a trypsin solution prepared by dissolving 0.005 g of trypsin (Sigma-Aldrich Co.) in 1 mL of 3$^{rd}$ distilled sterile water were introduced into an Eppendorf tube and, after vortexing for 20 minutes, reaction was carried out in an incubator at 37° C. for 3 hours. Finally, it was determined as to whether or not mutagenic activity had disappeared.

A sonicated *Lactobacillus* material having mutation inhibitory effects observed after protease treatment was passed through a 10 KDa membrane filter (Molecular Weight Cut-Off; Millipore, USA) and centrifuged at 4° C. with 14,000×g for 30 minutes, and then passed through a 3 KDa membrane filter and centrifuged at 4° C. with 14,000×g for 100 minutes, in turn obtaining an extract. Mutation inhibitory effects were monitored in different sectional regions of more than 10 KDa, 3 to 10 KDa, and less than 3 KDa.

As a result, the extract in the region of more than 10 KDa did not show antimutagenic activity while the extract in the region of less than 3 KDa exhibited antimutagenic activity of 50%. In addition, the extract in the region of 3 to 10 KDa had antimutagenic activity of −6.31%. The results are shown in TABLE 5. Consequently, it was found from the foregoing results that *Lactobacillus* sp. JNU2116 expressed antimutagenic effects in only a proteinous material having a molecular weight of less than 3 KDa.

TABLE 5

Identification of antimutagenic activity of *Lactobacillus* sp. JNU2116 cytoplasm component using mutagen IQ as well as *Salmonella Typhimurium*

| Sample | Revertant/plate (inhibitory rate %) |
|---|---|
| Control | 157 ± 10 |
| Natural revertant (spontaneous) | 88 ± 8 |
| 3 to 10 KDa | 161 ± 1 (−6.31%) |
| Less than 3 KDa | 123 ± 1 (50%) |

(3) Tricine SDS Electrophoresis

In order to measure a protein molecular weight of *Lactobacillus* sp. JNU2116, Tricine-sodium dodecyl sulfate-polyacryl amide gel electrophoresis (Tricine SDS-PAGE) was performed at 120V for 90 minutes according to Schand Jagow method (1987). The gel comprises 16.5% separate gel, 10% spacer gel and 4% stacking gel. As a standard molecular weight substance, polypeptide SDS-PAGE standard (Bio-Rad Laboratories, Hercules, Calif., USA) was used. A sample buffer was prepared of 2×(0.5M Tris-HCl pH 6.8, Glycerol, 10% SDS, β-mercaptoethanol, DW) and used. The sample and the buffer were admixed in a relative ratio of 1:1, heated in a boiling water for 5 minutes and subjected to electrophoresis. As a buffer for electrophoresis, a cathode buffer (0.1M Tris, 0.1M Tricine, 0.1% sodium dodecyl sulfate) and an anode buffer (0.2M Tris, pH 8.9) were used. After electrophoresis (PowerPaca Basic™, Bio-rad Co.), the gel was colored by silver staining.

Figure 3:
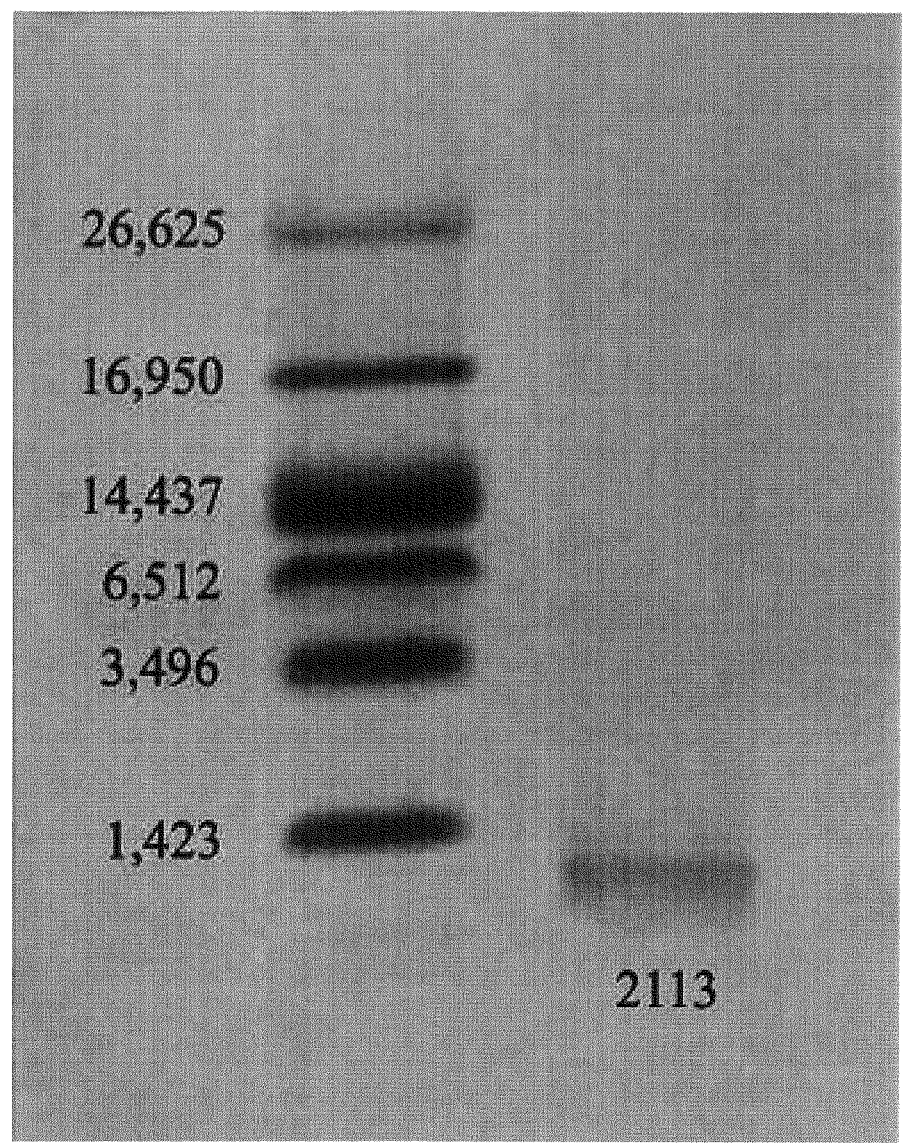
FIG. 3 illustrates electrophoresis results showing sizes of protein bands after protease treatment of *Lactobacillus* sp. JUN2116.

As shown in FIG. 3, protein bands were detected. A first lane shows a polypeptide SDS-PAGE standard wherein six protein bands are present between 1,423 Da to 26,625 Da. A band of *Lactobacillus* sp. JNU2116 was exhibited a little below 1,423 Da. By use of a Curve-fitting program, a molecular weight of the protein was calculated. When relative mobility of a standard protein was evaluated, a mobility of *Lactobacillus* sp. JNU2116 was about 8.6 cm and it was presumed that a substance influencing antimutagenic activity is a proteinous compound having a molecular weight of about 762 Da.

Analysis of N-terminal Sequence

A gel obtained after electrophoresis was blotted on a polyvinylidene difluoride membrane (PVDF; MSI, Westboro, Mass., USA). A part of the membrane which is expected to comprise a protein band with antimutagenic activity was cut and subjected to protein decomposition by Edmann method, then, analysis of protein sequence (Applied Biosystems Inc., CA, USA).

As a result of analyzing the membrane, a specific amino acid sequence of peptide, X-Leu-Glu-X-Lys-Lys-Ala-Glu-X-Ile-Thr-Thr-X-X, was identified.

What is claimed is:

1. A biologically pure *Lactobacillus* sp. JNU 2116 having a sequence represented by SEQ ID No: 1, the accession number of the deposit of the *Lactobacillus* sp. JNU 2116 being KCCM11055P.

2. A composition comprising the *Lactobacillus* sp. JNU 2116 as set forth in claim 1.

3. The composition of claim 2, wherein the composition is a pharmaceutical composition.

4. A food comprising the *Lactobacillus* sp. JNU 2116 as set forth in claim 1.

5. The food of claim 4, wherein the food is a fermented food.

6. A protein having an amino acid sequence represented by SEQ ID No: 2, wherein the protein is isolated from the N-terminal of *Lactobacillus* sp. JNU 2116 as set forth in claim 1.

* * * * *